| United States Patent [19] | [11] Patent Number: 4,632,979 |
| Coy et al. | [45] Date of Patent: Dec. 30, 1986 |

[54] THERAPEUTIC LHRH ANALOGS

[75] Inventors: David H. Coy, New Orleans, La.; Jacques-Pierre Moreau, Upton, Mass.

[73] Assignee: Tulane Educational Fund, New Orleans, La.

[21] Appl. No.: 621,673

[22] Filed: Jun. 18, 1984

[51] Int. Cl.$^4$ .............................................. C07K 7/20
[52] U.S. Cl. ...................................... 530/313; 514/800
[58] Field of Search .............. 260/112.5 LH; 530/313; 514/800

[56] References Cited

U.S. PATENT DOCUMENTS

| 4,010,125 | 3/1977 | Schally | 260/112.5 LH |
| 4,010,149 | 3/1977 | Baba et al. | 530/313 |
| 4,018,726 | 4/1977 | Schally et al. | 530/313 |
| 4,034,082 | 7/1977 | Johnson et al. | 530/313 |
| 4,071,622 | 1/1978 | Johnson | 424/177 |
| 4,218,439 | 8/1980 | Rivier | 260/112.5 LH |
| 4,234,571 | 11/1980 | Nestor et al. | 260/112.5 LH |
| 4,321,260 | 3/1982 | Auclair | 260/112.5 LH |

OTHER PUBLICATIONS

Schally (1971) *Biochem. Biophys. Res. Comm.* 43: 393, 1334.
Tolis (1982) PNAS 79: 1658–1662.
Borgmann, The Lancet, May 15, 1982, pp. 1097–1099.
Redding (1982) PNAS 79: 1273–1276.

*Primary Examiner*—Delbert R. Phillips

[57] ABSTRACT

A compound having the formula K-His-Trp-Ser-Tyr-M-Q-Arg-Pro-T, wherein K is N-Acetyl-Sarconsine or pGlu; is D-Phe, D-Trp, D-$\beta$-Naphthylalanine, or D-4-X-Phe, wherein X is OH, F, Cl, Br, or Me; Q is Leu, Phe, 4-X-Phe, Trp, or $\beta$-Naphthylamine (wherein X is OH, F, Cl, Br, or Me), or an N-Me-derivative thereof; and T is Gly-NH$_2$, NHCH$_3$, NHCH$_2$CH$_3$, or NHCH$_2$CH$_2$CH$_3$; provided that, when Q is Leu or N-Me-Leu, K cannot be pGlu; or a pharmaceutically acceptable salt thereof.

4 Claims, No Drawings

THERAPEUTIC LHRH ANALOGS

BACKGROUND OF THE INVENTION

This invention relates to amino acid-containing therapeutic compounds.

Luteinizing hormone (LH) and follicle-stimulating hormone (FSH) are gonadotropic hormones produced by the pituitary gland of humans and animals. LH and FSH are released from the pituitary gland by the action of LH- and FSH-releasing hormone (LHRH). Naturally-occuring LHRH has been shown to be a decapeptide of the formula (pyro)-Glu-His-Trp-Ser-Tyr-Gly-Leu-Arg-Pro-Gly-$NH_2$; A. V. Schally et al., *Biochem. Biophys. Res. Comm.*, 43, 393 and 1334 (1971). (Herein, where no isomeric designation is given, the naturally occurring L-form is meant.)

A large number of patents and publications described LHRH analogs and their use in various medical applications. For example, Schally and Coy U.S. Pat. No. 4,010,125 describes a decapeptide analogue of LHRH of the formula (pyro)-Glu-His-Trp-Ser-Tyr-D-Trp-Leu-Arg-Pro-Gly-$NH_2$ useful for inducing ovulation and for treating delayed puberty and hypogonadism.

Tolis et al. *Proc. Natl. Acad. Sci.* 79, 1658–1662 (1982) suggests that the chronic administration of large doses of two LHRH analogues ([D-$Trp^6$] LHRH and [D-Ser(But)$^6$]des-Gly-$NH_2{}^{10}$-LHRH) can result in the suppression of pituitary and leydig cell production and the regression of mammary and prostatic endocrine-dependent tumors in animals and humans.

Johnson et al. U.S. Pat. No. 4,071,622 describes nonapeptides of the formula pGlu-His-Trp-Ser-Tyr-X-Leu-Arg-Pro-NH-$C_2H_5$, where X is the D form of Tyr, Trp, or Phe, useful for the treatment of mammary tumors.

SUMMARY OF THE INVENTION

In general, the invention features compounds having the formula K-His-Trp-Ser-Tyr-M-Q-Arg-Pro-T, wherein K is N-acetyl-Sarcosine or pGlu; M is D-Phe, D-Trp, D-$\beta$-Napthylalanine, or D-4-X-Phe, wherein X is OH, F, Cl, Br, or Me; Q is Leu, Phe, 4-X-Phe, Trp, or $\beta$-Napthylalanine, wherein X is as defined above, or an N-Me-derivative thereof; and T is Gly-$NH_2$, $NHCH_3$, $NHCH_2CH_3$, or $NHCH_2CH_2CH_3$; provided that, when Q is Leu or N-Me-Leu, K cannot be pGlu; or a pharmaceutically acceptable salt thereof.

Preferred compounds of the invention are N-Acetyl-Sarcosine-His-Trp-Ser-Tyr-D-Phe-Leu-Arg-Pro-$NHCH_2CH_3$; pGlu-His-Trp-Ser-Tyr-D-Phe-Phe-Arg-Pro-Gly-$NH_2$; pGlu-His-Trp-Ser-Tyr-D-Trp-Leu-Arg-Pro-$NHCH_2CH_3$; N-Acetyl-Sar-His-Trp-Ser-Tyr-D-Trp-Leu-Arg-Pro-$NHCH_2CH_3$; and N-Acetyl-Sar-His-Trp-Ser-Tyr-D-Trp-Leu-Arg-Pro-Gly-$NH_2$.

In other preferred embodiments, a therapeutically effective amount of the therapeutic compound and a pharmaceutically acceptable carrier substance, e.g. a sterile aqueous vehicle which may also contain other solutes such as buffers or preservatives, polyethyleneglycol, lactose, or silica, together form a therapeutic composition e.g. a pill, tablet, or capsule for oral administration to a human patient, a powder or liquid capable of being administered nasally as drops of spray, or a solid or liquid carrier capable of being injected intramuscularly or implanted for prolonged periods of time in long-acting, slow release, or depot dosage forms.

The pill, tablet or capsule can be coated with a substance capable of protecting the composition from the gastric acid in the patient's stomach for a period of time sufficient to allow the composition to pass undisintegrated into the patient's small intestine.

The compounds of the invention can be effective in treating hormone-dependent cancers as well as alleviating the adverse effects of chemotherapy-induced hormone suppression. Furthermore, their low molecular weight facilitates administration and absorption.

Other features and advantages of the invention will be apparent from the following description of the preferred embodiments thereof, and from the claims.

DESCRIPTION OF THE PREFERRED EMBODIMENT

Structure

The compounds of the invention have the general formula recited in the Summary of the Invention above. Examples of preferred compounds within the general formula are those referred to as preferred embodiments above.

The compounds are nonapeptide or decapeptide LHRH analogs. The compounds can be provided in the form of acid addition salts, e.g., salts of organic acids, such as acetic, lactic, succinic, benzoic, salicyclic, methanesulfonic or toluenesulfonic acid; polymeric acids such as tannic acid or carboxymethyl cellulose; and inorganic acids such as hydrohalic acids, e.g., hydrochloric acid, sulfuric acid, or phosphoric acid.

If desired, a particular acid addition salt can be converted into another acid addition salt, e.g. a salt with a non-toxic, pharmaceutically acceptable acid, by treatment with the appropriate ion exchange resin, e.g., in the manner described in Boisonnas et al., *Helv. Chim. Acta*, 43, 1349 (1960), hereby incorporated by reference. Suitable ion exchange resins are cellulose based cation exchangers, e.g., carboxymethylcellulose or chemically modified, cross linked dextran cation exchangers (such as Sephadex C-type), and strongly basic anion exchange resins, (such as those listed in Greenstein et al., "Chemistry of the Amino Acids", John Wiley and Sons, Inc., New York and London, 1961, Vol. 2, p. 1456).

Synthesis

The compounds of the invention can be prepared using solid phase synthesis. Synthesis is preferably commenced at the C-terminal end of the peptide using an $\alpha$-amino protected resin of the C-terminal amino acid. Such a starting material is prepared by attaching an $\alpha$-amino protected proline or glycine (depending on the peptide) to a benzhydrylamine resin, or a chloromethylated resin. The preparation of the benzhydrylamine resin is described in Rivaille et al., *Helv. Chim. Acta*, 54, 2772 (1971) and the chloromethylated resin is commercially available from BioRad Laboratories, Richmond, Calif.

In using the benzhydrylamine resin, an amide anchoring bond is formed with the $\alpha$-amino protected amino acid as follows:

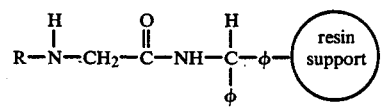

This permits the C-terminal amide function to be obtained directly after the synthesis of the amino acid sequence has been completed, by cleaving off the resin support of the linked peptide to form the amide at the C-terminal portion of the desired peptide. In this instance the use of hydrogen fluoride for cleaving off the resin support also advantageously removes the side chain protective groups.

When chloromethylated resin is used, the anchoring bond is the benzylester group. In this instance a convenient procedure for converting the linked protected peptide to the C-terminal amide is to immonolize the protected peptide off the resin and then remove the protective groups of the resulting amide by treatment with sodium and liquid ammonia or by hydrogen fluoride cleavage. An alternative procedure is to cleave by transesterification with a lower alkanol, preferably methanol or ethanol. In the presence of triethylamine and then convert the resulting ester into an amide and subsequently deprotect as described above.

More specifically, to make peptides having a C-terminal glycine, an α-amino protected glycine, preferably t-butyloxy-carbonylglycine (boc-gly), is coupled to benzhydrolamine resin with the aid of a carboxyl group activating compound, preferably dicyclohexylcarbodiimide. Following the coupling of the α-amino protected glycine to the resin support, the α-amino protecting group is removed, e.g., using trifluoroacetic acid in methylene chloride, trifluoroacetic acid alone, or hydrochloric acid in dioxane. Deprotection is carried out at a temperature between about 0° C. and room temperature. Other standard cleaving reagents and conditions for removal of specific α-amino protecting groups can be used, as described in Schroder et al., "The Peptides", Vol. 1, Academic Press, New York, 1965, pp. 72–75.

After removal of the α-amino protecting group, the remaining α-amino protecting amino acids are coupled step-wise in the desired order to obtain the desired peptide. Each protected amino acid is introduced into the solid phase reactor in about a three-fold excess and coupling is carried out in methylene chloride or dimethylformamide in methylene chloride. In cases where incomplete coupling occurs, the coupling procedure is repeated before removal of the α-amino protecting group, prior to the coupling of the next amino acid to the sollid phase reactor. The success of the coupling reaction at each stage of the synthesis can be monitored by the ninhydrin reaction, as described in Kaiser et al., *Analyt. Biochem.* 34, 595 (1970).

Although a solid phase synthesis of the peptides is preferred, classical methods can also be used, as described, e.g., in Immer et al. U.S. Pat. No. 3,853,108.

Specific compounds are prepared as follows.

N-acetyl-sarcosine-N$^{im}$-tosyl-histidine-tryptophan-O-benzyl-serine-tyrosine-D-phenylalanine-leucine-N$^G$-tosyl-arginine-proline-ethylamide Boc-Pro is esterified to chloromethylbenzyl-poly-styrene resin (1% cross-linked with divinylbenzene) (Bio Rad) to give a Boc-Pro-resin with an incorporation of 0.5 mmole of Pro per gram.

This resin (2.0 g, 1.0 mmole) is placed in the reaction vessel of a Beckman 990 automatic peptide synthesizer programmed to carry out the following work-wash cycle: (a) CH$_2$Cl$_2$; (b) 33% trifluoroacetic acid in CH$_2$Cl$_2$ (2 times for 1 min. and 25 min. each); (c) CH$_2$Cl$_2$; (d) C$_2$H$_5$OH; (e) CH$_2$Cl$_2$; (f) 10% (C$_2$H$_5$)$_3$N in CH$_2$Cl$_2$.

The neutralized resin is stirred with Boc-N$^G$-tosyl-arginine [Boc-Arg(Tos)] and diisopropylcarbodiimide (3.0 mmole) in CH$_2$Cl$_2$ for 1 h and the resulting amino acid resin is then cycled through steps (a) through (g) in the above wash program. The following amino acids (3.0 mmole) are then coupled successively by the same reaction cycle: Boc-Leu, Boc-D-Phe, Boc-Tyr, Boc-Ser(Bzl), Boc-Trp, Boc-His(Tosyl), acetyl Sar. The completed peptide-resin (3.71 g) is then suspended in DMF (20 ml) to which is added ethylamine (5 ml) at 0° C. The mixture is stirred at room temperature and filtered to remove spent resin. The filtrate is evaporated to a yellow oil which solidifies to give the protected peptide as an off-white powder (590 mg).

N-Ac-sarcosine-histidine-tyrptophan-serine-tyrosine-D-phenylalanine-leucine-arginine-proline-ethylamide The above protected peptide (590 mg) is mixed with anisole (4 ml), dithiothreitol (100 mg) and anhydrous hydrogen fluoride (36 ml) at 0° C. and stirred for 45 min. Excess hydrogen fluoride is evaporated rapidly under a stream of dry nitrogen and the free peptide is precipitated and washed with ether. The peptide is then dissolved in a minimum volume of 2M AcOH and eluted on a column (2.5 × 100 cm) of Sephadex G-25. Fractions containing a major peak observed at 280 nm are pooled and lyophilized. This material is then applied to a column (2.5 × 50 mm) of Whatman octadecylsilane-silica (LRP-1, 15–20 μM) which is eluted with a linear gradient of 10–50% acetonitrile-0.1% trifluoroacetic acid in water. Fractions are examined by thin layer chromatography and high pressure liquid chromatography and pooled to give maximum purity. Lyophilization of the solution gives 138 mg of the product as a fluffy white powder.

The product is found to be homogeneous by thin layer chromatography in 4 solvent systems on silica gel plates. Amino acid analysis of an acid hydrolysate confirms the composition of the peptide.

N-Acetyl-sarcosine-histidine-tryptophan-serine-tyrosine-D-tryptophan-leucine-arginine-proline-ethylamide The above peptide is prepared in the same fashion as N-Ac-Sar-His-Trp-Ser-Tyr-D-Phe-Leu-Arg-Pro-NHCH$_3$CH$_3$ by using Boc-D-Trp instead of Boc-D-Phe during the amino acid coupling step.

Pyroglutamic acid-histidine-tryptophan-serine-tyrosine-D-phenylalanine-phenylalanine-arginine-proline-glycine-amide Benzhydrylamine polystyrene resin (Bachem, Inc.) (1.58 g, 0.50 mmole) in the chloride ion form is placed in the reaction vessel of the automatic peptide synthesizer and subjected to the work-wash cycle described above. The following amino acids (1.5 mmole) are then coupled under the conditions described above: Boc-Gly, Boc-Pro, Boc-Arg (Tos), Boc-Phe, Boc-D-Phe, Boc-Tyr, Boc-Trp, Boc-His (Tos), pGlu. The completed resin weights 2.06 g.

The resin is cleaved by the hydrogen fluoride treatment described above and the free peptide is extracted into a minimum volume of 2M AcOH. The purification schedule described above then gives pure peptide (140 mg) as a white, fluffy powder.

This material is found to be homogeneous by analytical thin layer chromatography in 4 solvent systems on silica gel plates. Amino acid analysis of an acid hydrolysate confirms the composition of the peptide.

N-Acetyl-sarcosine-histidine-tryptophan-serine-tyrosine-D-tryptophan-leucine-arginine-proline-glycine-amide Benzhydrylamine polystyrene resin (Bachem, Inc.) (1.58 g, 0.50 mmole) in the chloride ion form is placed in the reaction vessel of the automatic peptide synthesizer and subjected to the work-wash cycle described above. The following amino acids (1.5 mmole) are then coupled under the standard conditions. Boc-Gly, Boc-Pro, Boc Arq (Tos), Boc-Leu, Boc-D-Trp, Boc-His (Tos), acetyl Sar. The completed resin weights 2.10 g.

The resin is cleaved by the hydrogen fluoride treatment described above and is purified as described above to give 152 mg of the pure compound as a white, fluffly powder.

This material is found to be homogeneous by analytical thin layer chromatography in 4 solvent systems. Amino acid analysis of an acid hydrolysate conforms the composition of the peptide.

pGlu-His-Trp-Ser-Tyr-D-Trp-Leu-Arg-Pro-Gly-NHCH$_2$CH$_3$

This decapeptide is prepared in a manner analogous to those described above.

Use

The peptides of the invention can be administered, preferably in the form of an acid addition salt in combination with a pharmaceutically acceptable carrier substance, to a human or animal patient in need of such peptide. An effective amount of the peptide can be administered systemically, either by intravenous, subcutaneous, or intramuscular injection, or by any other medically acceptable method, e.g., by oral, sublingual, or nasal administration.

The peptides can be used to treat reproductive system-related disorders, e.g., precocious puberty. The peptides can also be administered to male sex offenders to decrease testosterone levels and thus diminish sex drive, and to humans, preferably women, as a contraceptive. The peptides can also be used to minimize deleterious effects during chemotherapy treatment for cancer by temporarily and reversibly suppressing hormone levels. The peptides can also be used to treat endometriosis, pencreatic cancer, and hormone-dependent cancers, e.g. prostate, breast, thyroid, and ovarian cancer. (A hormone-dependent cancer is a cancer whose virulence can vary with hormone level.) The peptides can also be used to treat benign prostrate hyperplasia.

The mechanism by which the compounds inhibit tumor growth is believed to be either inhibition of trophic hormones such as testosterone, or a direct effect on the tumor itself.

An advantage of the compounds is that they can lower testosterone levels in mammals over time while causing a fairly low initial "flare up", or increase, in testosterone levels.

The mode of administration of the peptides may vary with use. For example, the preferred mode of administration for treatment of cancer will be to include the peptide in an implant of, e.g. a biodegradable polymer, which is transdermally implanted in the cancer patient for prolonged release of the peptide over time.

Dosage will also vary with application, and will generally be higher for cancer therapy than for contraceptive and other therapeutic uses. Generally, the dosage for non-cancer use will be between 1 and 50 micrograms/kg/day, preferably about 10 micrograms/kg/day. Dosage for treatment of cancer will be between 10 and 500 micrograms/kg/day, preferably about 100 micrograms/kg/day.

Other embodiments are within the following claims.

We claim:

1. The compound having the formula N-Ac-Sarc-His-Trp-Ser-Tyr-D-Phe-Leu-Arg-Pro-NHCH$_2$CH$_3$.

2. The compound having the formula pGlu-His-Trp-Ser-Tyr-D-Phe-Phe-Arg-Pro-Gly-NH$_2$.

3. The compound having the formula N-Ac-Sar-His-Trp-Ser-Tyr-D-Trp-Leu-Arg-Pro-Gly-NH$_2$.

4. The compound having the formula N-Ac-Sar-His-Trp-Ser-Tyr-D-Trp-Leu-Arg-Pro-NHCH$_2$CH$_3$.

* * * * *

UNITED STATES PATENT AND TRADEMARK OFFICE
CERTIFICATE OF CORRECTION

PATENT NO. : 4,632,979
DATED : December 30, 1986
INVENTOR(S) : David H. Coy et al.

It is certified that error appears in the above-identified patent and that said Letters Patent is hereby corrected as shown below:

COLUMN 1,

As a first sentence and paragraph, insert the paragraph:

--This invention was made in the course of work under a grant or award from the U.S. government; therefore, the U.S. government has rights in the invention.--

Signed and Sealed this

Eighteenth Day of August, 1992

Attest:

DOUGLAS B. COMER

Attesting Officer

Acting Commissioner of Patents and Trademarks